US012564397B2

(12) United States Patent
McMahon

(10) Patent No.: US 12,564,397 B2
(45) Date of Patent: *Mar. 3, 2026

(54) SURGICAL DEVICE FOR COMPLEX SUTURING FIBROUS TISSUES

(71) Applicant: Patrick J. McMahon, Pittsburgh, PA (US)

(72) Inventor: Patrick J. McMahon, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/673,768

(22) Filed: May 24, 2024

(65) Prior Publication Data

US 2024/0307054 A1 Sep. 19, 2024

Related U.S. Application Data

(63) Continuation of application No. 17/452,956, filed on Oct. 29, 2021, now Pat. No. 12,004,736, which is a continuation of application No. 16/391,432, filed on Apr. 23, 2019, now Pat. No. 11,160,548.

(60) Provisional application No. 62/717,402, filed on Aug. 10, 2018.

(51) Int. Cl.
*A61B 17/04* (2006.01)
*A61B 17/06* (2006.01)

(52) U.S. Cl.
CPC .... *A61B 17/0469* (2013.01); *A61B 17/06066* (2013.01); *A61B 2017/06095* (2013.01)

(58) Field of Classification Search
CPC .......... A61B 17/0469; A61B 17/06066; A61B 17/0482; A61B 17/0485; A61B 2017/06095
See application file for complete search history.

(56) References Cited

U.S. PATENT DOCUMENTS

2011/0118760 A1* 5/2011 Gregoire ............ A61B 17/0469
606/145

* cited by examiner

*Primary Examiner* — Sarah A Long
(74) *Attorney, Agent, or Firm* — Anton J. Hopen; Trenam Law

(57) ABSTRACT

Instruments for placing complex sutures into animal tissues, including instruments useful in arthroscopic surgical techniques which minimize incision size. The instruments manipulate tissue by, for example, rolling, wrinkling, folding, bending, or tucking the tissue so that a needle can be placed through the tissue more than once. Sutures are placed, for example from top-to-bottom and bottom-to-top with a single pass of a straight needle. In addition, the instruments can roll, wrinkle, fold, bend, or tuck the flat tissue so that a needle can be placed through the tissue more than once and a loop can be sutured through the tissue so that another suture can pass through resulting in sewing both sides of the tissue. This will allow surgeons to place complex locking and grasping suture configurations that will significantly improve the repair.

18 Claims, 23 Drawing Sheets

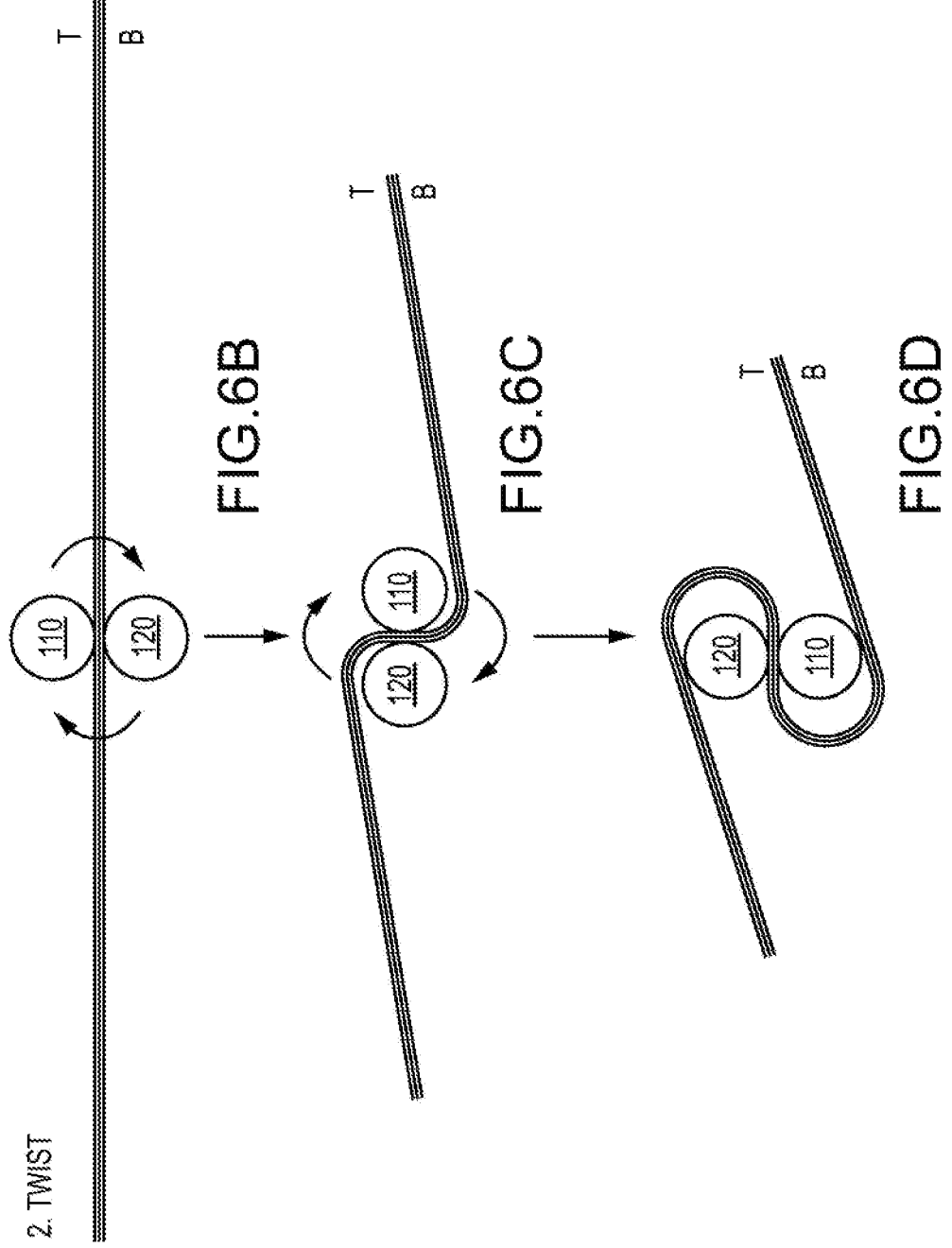

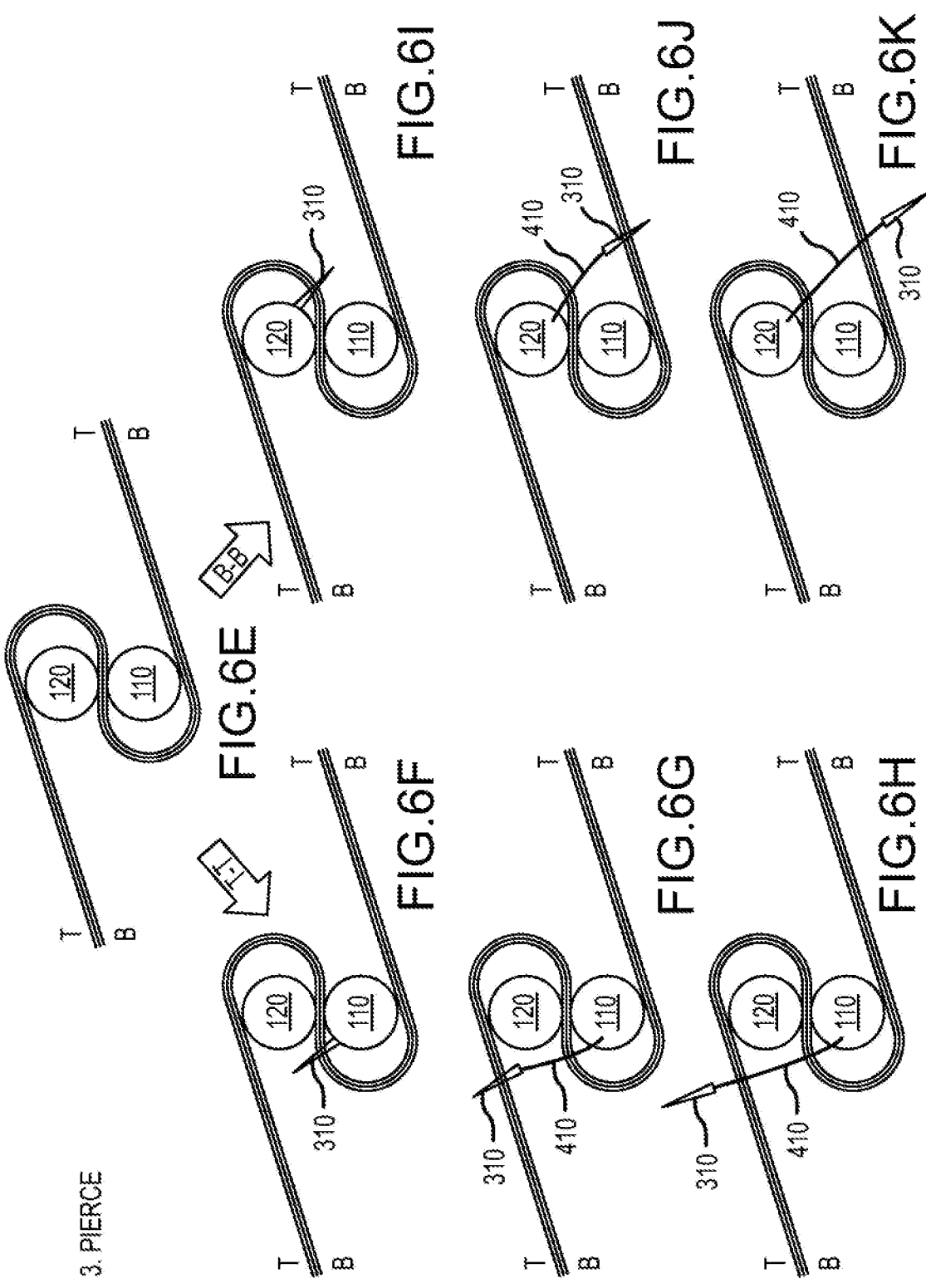

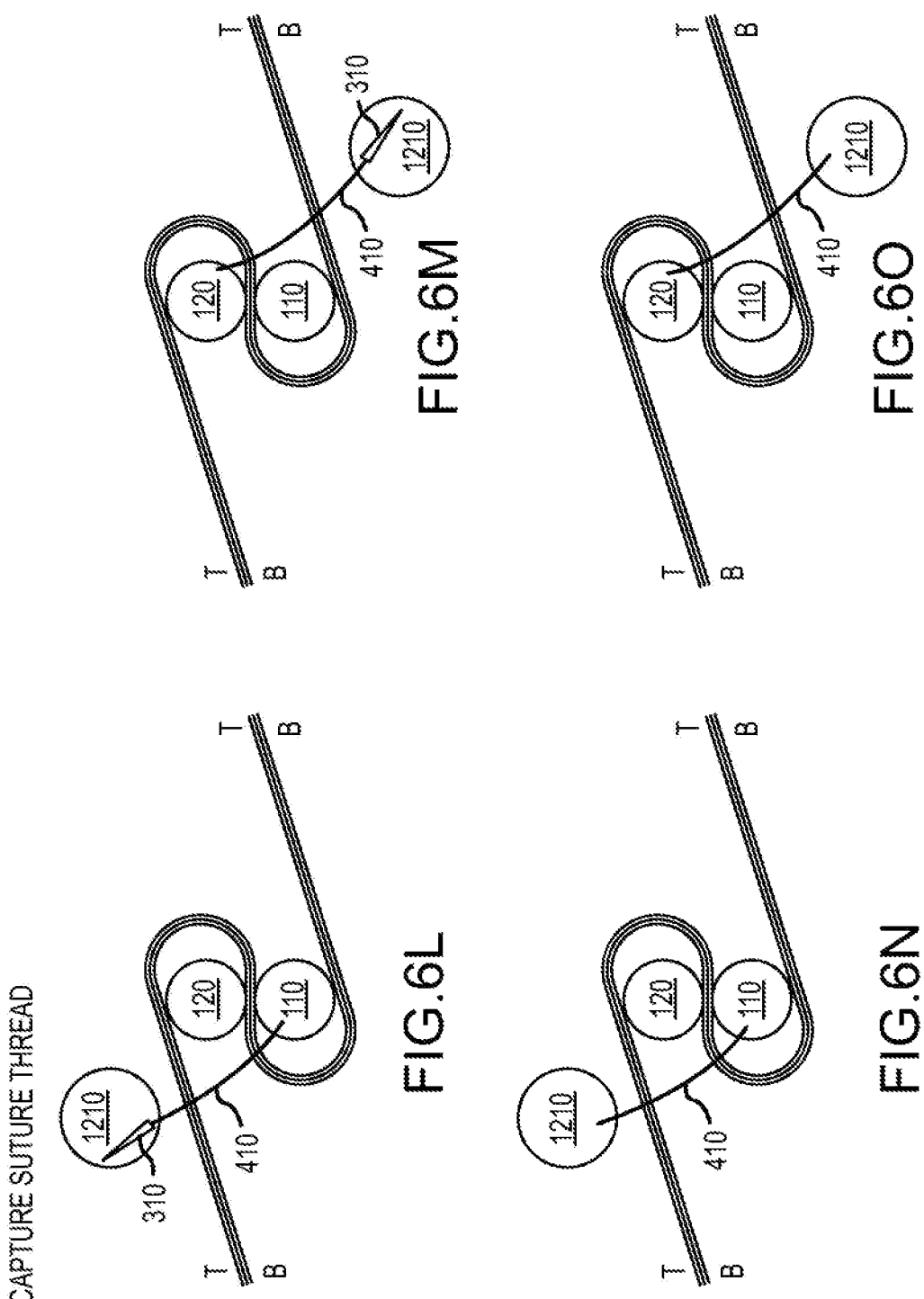

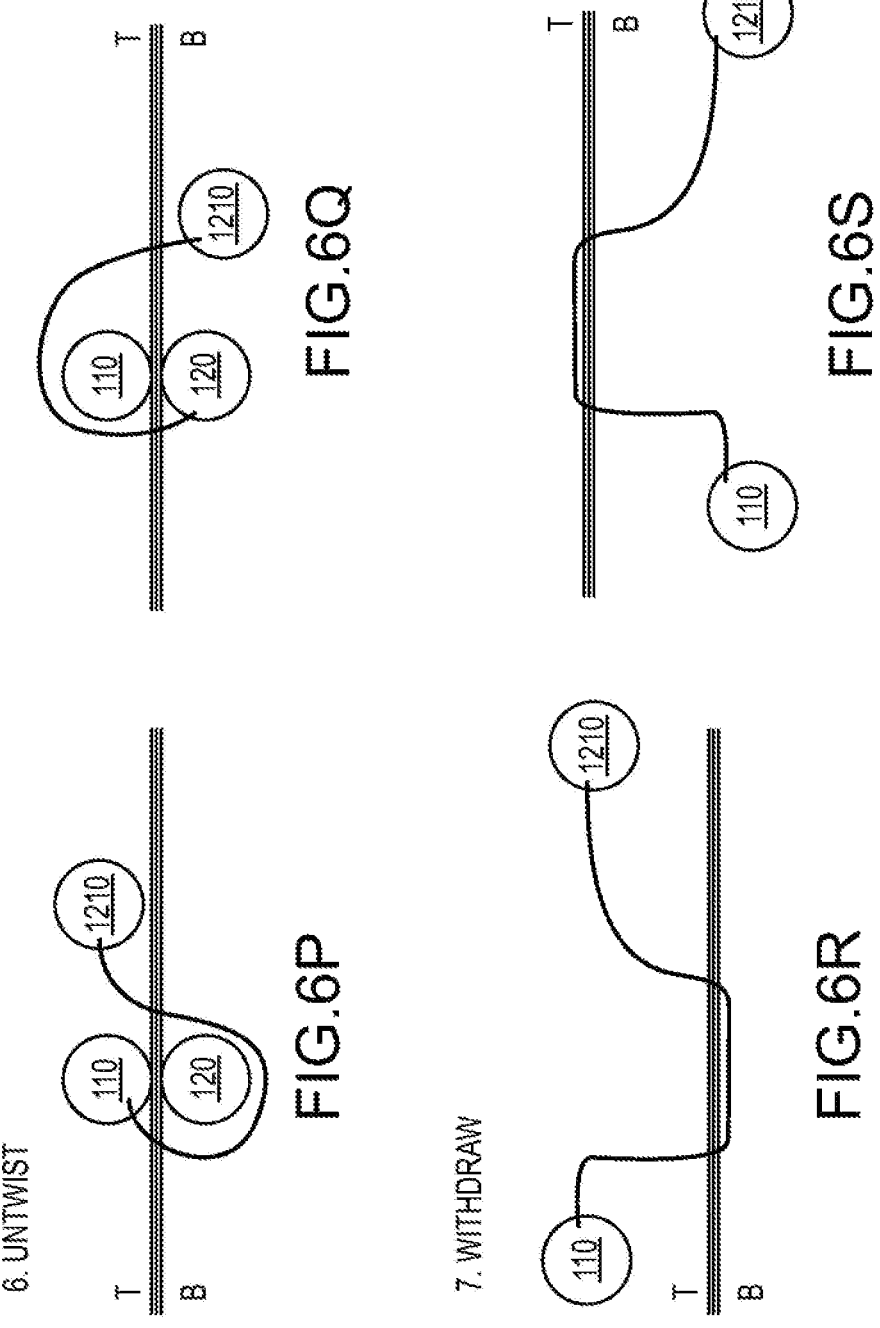

11. CAPTURE SUTURE THREAD AGAIN

FIG.6W

12. UNTWIST AND WITHDRAW AGAIN

FIG.6X

12 ALT?. UNTWIST AND WITHDRAW AGAIN

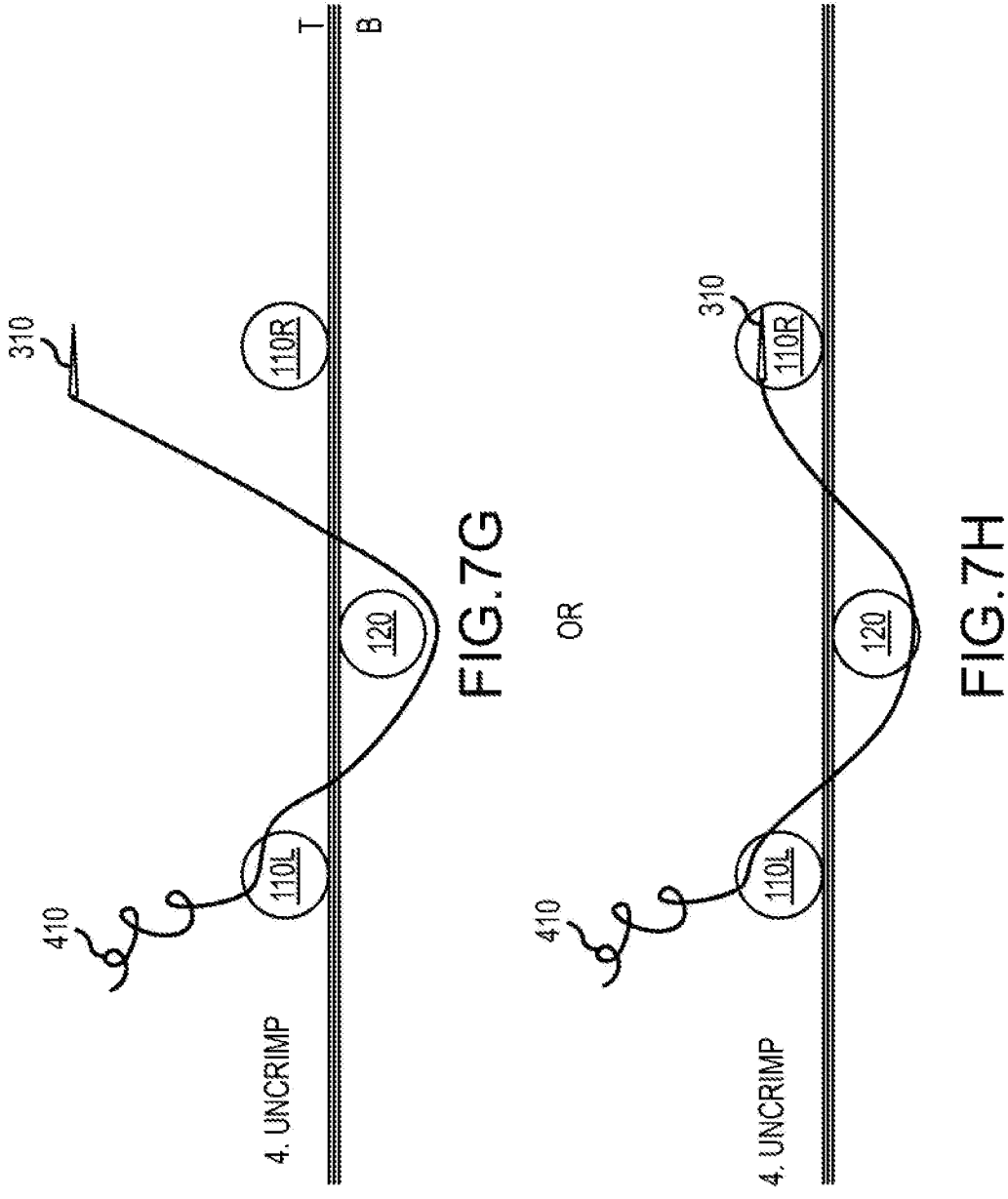

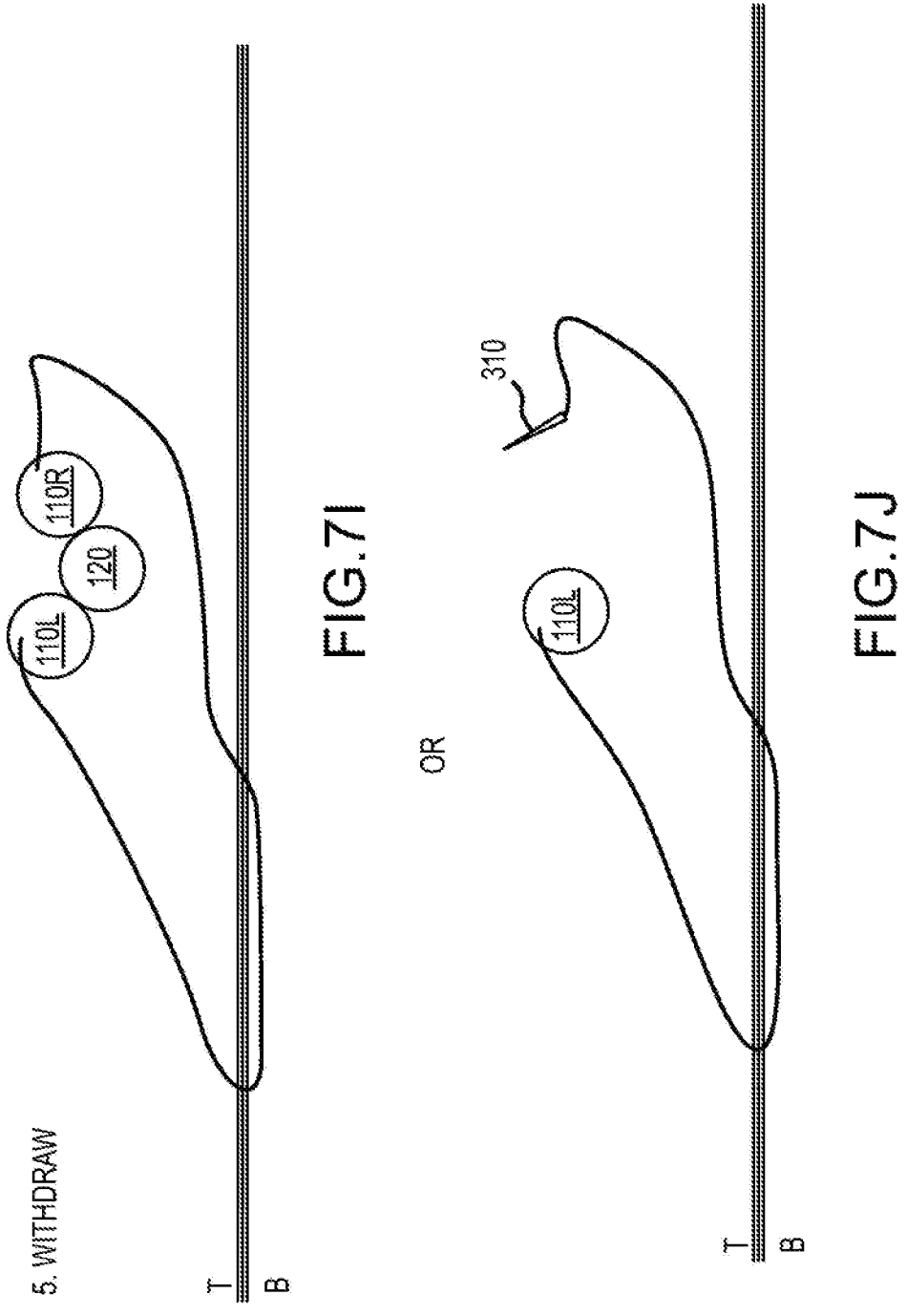

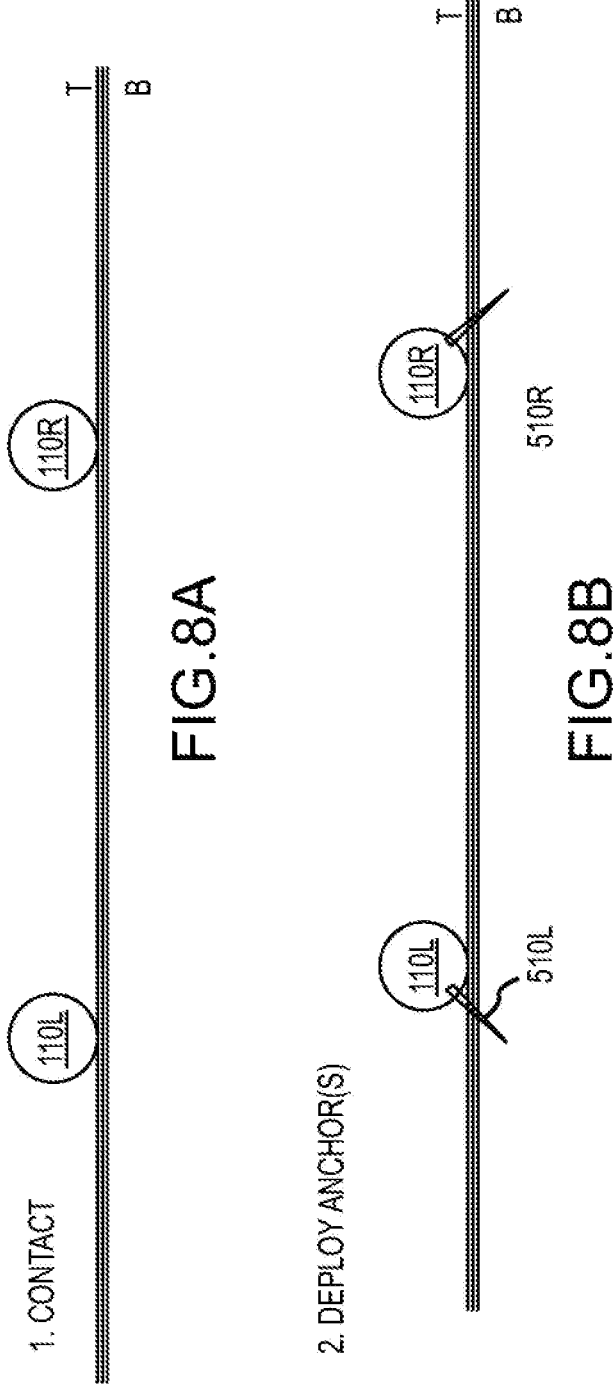

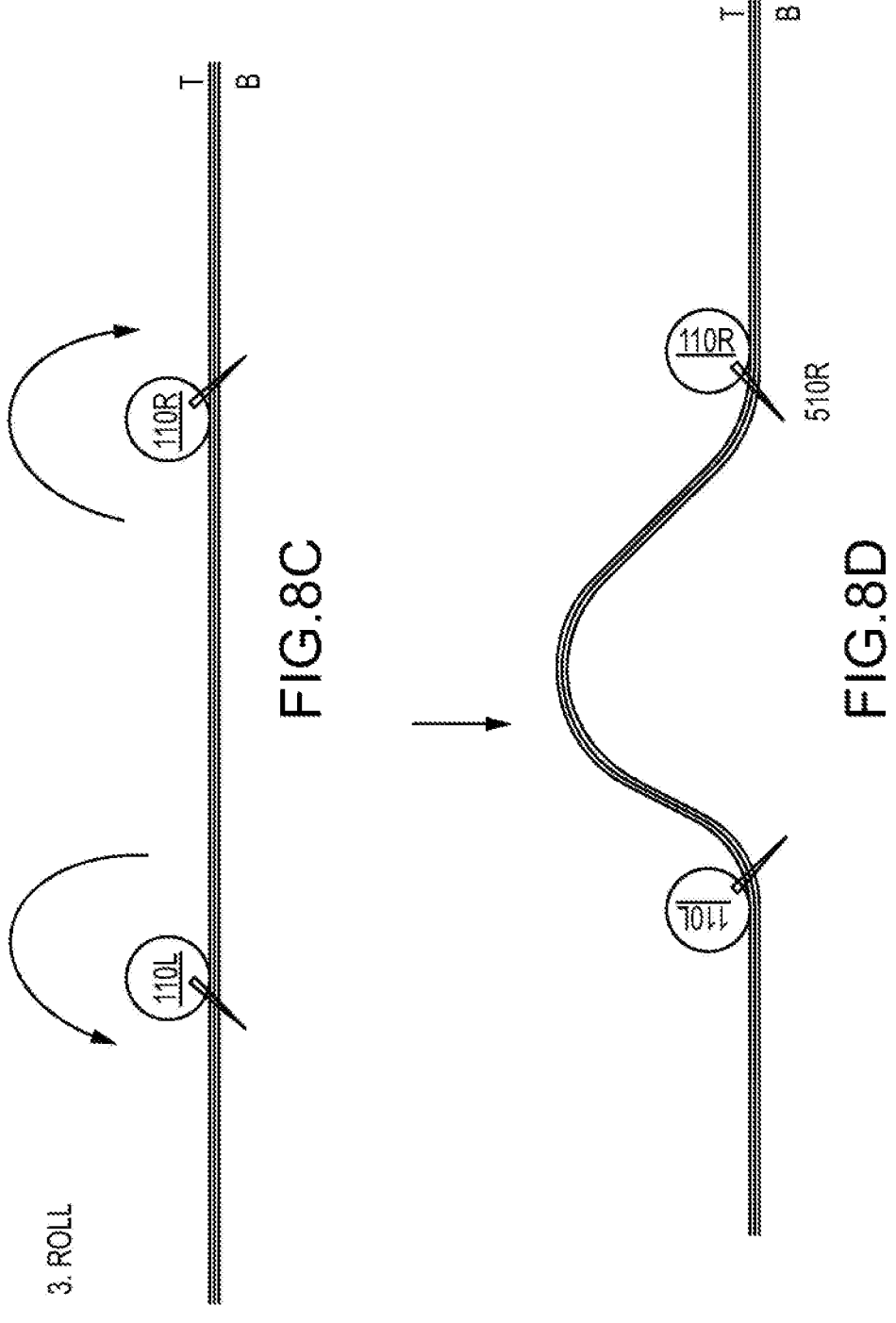

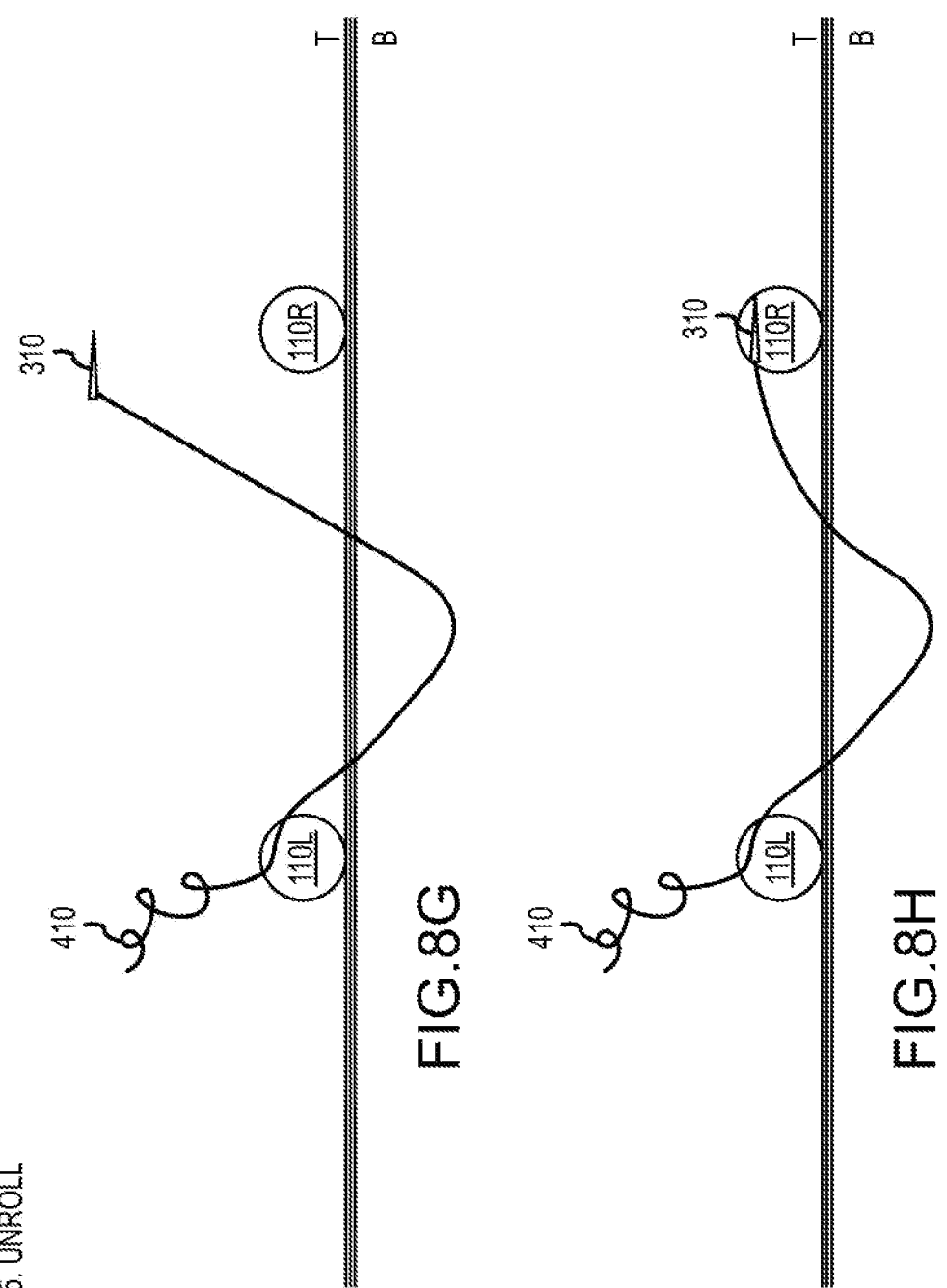

SURGICAL DEVICE FOR COMPLEX SUTURING FIBROUS TISSUES

CROSS-REFERENCE TO RELATED APPLICATIONS

This nonprovisional application is a continuation of and claims priority to nonprovisional application Ser. No. 17/452,956, entitled "Surgical Device For Complex Suturing Fibrous Tissues," filed Oct. 29, 2021 by the same inventor, which is a continuation of and claims priority to nonprovisional application Ser. No. 16/391,432, entitled "Surgical Device For Complex Suturing Fibrous Tissues," filed Apr. 23, 2019 by the same inventor, which claims the benefit of U.S. Provisional 62/717,402, filed Aug. 10, 2018, which is hereby incorporated by reference as if submitted in its entirety.

BACKGROUND OF THE INVENTION

1. Field of the Invention

The disclosed relates generally to the field of surgical instruments, in particular instruments for placing complex sutures into human tissues, including instruments useful in cramped or tight surgical environments, such as arthroscopic, laparoscopic, "keyhole," and other incision-minimizing surgical techniques which minimize incision size.

2. Brief Description of the Prior Art

An example of applicable human tissue injuries are those of the rotator cuff that are the most common of shoulder injuries. About 25% of Americans over 60 years of age and 50% over 80 years of age have a full thickness rotator cuff tear. This is true even in senior athletes as over 20% of athletes over 60 years of age have a full thickness rotator cuff tear. And as the number of elderly Americans is rising each year, by the year 2025 there is estimated to be over 20 million individuals with a full thickness rotator cuff tear.

The rotator cuff is a stout 5 layered sheet-like tissue composed of mostly parallel collagen fibers that surround the glenohumeral joint and insert into the humeral head with mostly parallel collagen fibers that slide relative to one another. This allows large range of shoulder motion without wrinkles.

Over 250,000 rotator cuff repairs are performed by surgeons yearly in the United States. Healing occurs in only about 75% of these and is more of a problem •with severe rotator cuff tears. Despite advances such as arthroscopic surgical techniques, more sutures and suture anchors, healing after rotator cuff surgery is not much better today than it was 25 years ago. Today failure occurs predominantly with the sutures pulling out of the tissue. More complex suture configurations using running and locking stitches will diminish this mode of failure. This is the common technique for other tissues such as the flexor tissues of the hand and the Achilles tissue of the foot that are repaired with open surgical techniques.

Arthroscopic shoulder surgery results in decreased pain, infection, and iatrogenic injuries of the deltoid muscle. But too many patients have a poor outcome after their rotator cuff repairs and the main method by which the repair fails is the sutures pulling out of the tissue. A better suturing technique is needed for arthroscopic surgery but suturing the stout, sheet-like tissue is difficult. Current instruments use a needle to pass a suture through the tissue from bottom-to-top with simple, mattress or modified Mason-Allen suture configurations.

Most surgeons currently use a single arthroscopic sewing instrument during rotator cuff surgery such as the Mitek Express-sew or the Arthrex Scorpion. Both of these grasp above and under the tissue with one tip on the bottom through which a flexible needle passes a suture to the tip on top. The sutures can be placed through the tissue from bottom-to-top resulting in simple, mattress or Mason-Allen suture configurations.

Suturing biological tissues is a common technique for repairing tissues which have been severed as a result of injury or surgical incisions. Suturing involves inserting a suture material such as a silk, nylon, or polyethylene monofilament with a braided polyester sheath thread through a biological tissue, such as skin, muscle, tendon, or ligament. The tissue surrounding the suture material holds it within the tissue and permits the tissue to be manipulated through handling of the portions of the suture material extending beyond the tissue. For example, suturing is commonly used to close wounds of human skin by inserting a strand of suture material through skin portions on both sides of the wound, tensioning the ends of the suture material to transmit tensional force to the skin portions to draw them towards one another (e.g., abutting one another), and then tying the suture material into a knot to hold the skin portions in the tensioned position to permit healing of the wound that join the skin portions to one another.

Many suturing techniques are known and described, and particular suturing techniques are employed in different medical procedures, because the mechanical characteristics of the suturing technique and/or the resulting sutures are beneficial for healing, simple to perform, or both. By way of example, a common technique for closing skin wounds is to employ two pairs of skin punctures—one on either side of the wound—and to thread a single suture material through both punctures on one side (e.g., passing top-to-bottom through one puncture and bottom-to-top through the other), extending the suture across the wound, from one side to the other. When the suture material is tensioned (e.g., by pulling on its free ends prior to tying), the suture material extending through the sides of the wound distribute tension along the tissue in the direction of the suture material and further draw the two sides of the wounds toward one another prior to tying the suture material and this maintains the tension. This suture method favorably distributes tension along the wound, rather than focusing it at individual puncture sites, which tends to reduce the tendency of suture material to tear skin tissue at the puncture sites, stabilizing the wound and promoting healing.

The position at which and orientation with which a suture material is inserted through a biological tissue can have great significance. Sutures are often used to exert mechanical forces upon such tissues following suturing. By way of example, sutures ("stitches") can be used to hold skin portions on opposite sides of a skin tear or incision together to aid healing and reformation of an integral skin surface. Likewise, sutures can hold other tissues such as fibrous tissues (e.g., tendons, or ligaments) closely together or close against bone surfaces to aid healing.

Force(s) are exerted upon tissues by the suture material being tensioned (e.g., by surgeons and other medical personnel pulling the suture material and/or tying or otherwise fastening it). The type and number of sutures affect the quality of the repair and surgeons make decisions on these for the best repair. The orientation of the stitch also affects outcome as certain tissues will tend to tear more easily than other tissues when and after being sutured. The load to pull the suture out of the tissue varies for different tissues depending on the tissue size and composition. Sutures can pull out of thin, short tissues easier than thick, long tissues. And when the tissue composition is parallel collagen fibers, suture failure-pulling out-is more common than when the tissue is composed of matted collagen fibers. The flexor tissue of the finger for example has parallel collagen fibers so sutures can pull out of the repair when tensioned, resulting in poor outcomes more commonly than if it had matted collagen fibers like skin. Surgeons space sutures in configurations to optimize the quality of the repair and allow healing. Placing more sutures and doing so in complex suture configurations has resulted in best outcomes after flexor tendon repair. Placement of the suture is important in other tissues as well as within a single tissue (e.g., a strap-shaped tissue, such as one of the tissues of the human shoulder rotator cuff), different regions of the tissue can resist tearing during and after being sutured differently. Surgeons therefore tend to take care to suture tissues with suture orientation techniques and at positions which are able to resist tearing under the mechanical loads expected to be exerted upon the tissues.

Surgeons and surgical instrument designers know the quality of the repair and the opportunity for healing is affected by the type, number, orientation, spacing and placement of stitches in a repaired tissue as these as these.

When suturing in a cramped or tight surgical environment (such as are present in many arthroscopic, laparoscopic, "keyhole," and other incision-minimizing surgical techniques), the desired stitching technique can be more difficult than with open techniques with large incisions that allow ready access to the suture site. However, complications are more frequent with open techniques and recovery times can be longer so it is desirable to minimize these. A substantial need exists for surgical devices that allow a variety of techniques useful for suturing in cramped surgical environments.

Other examples of surgical procedures that would benefit from a surgical device for complex suturing in cramped or tight surgical environments are laparoscopic hernia repair, laparoscopic hysterectomy, and mini-incision plastic surgery.

The subject matter described herein overcomes at least some of these shortcomings of previously known surgical suturing devices and techniques.

BRIEF SUMMARY OF THE INVENTION

One or more of the disclosed embodiments repair, in this example, the rotator cuff with complex locking and grasping suture configurations that will significantly improve the load to re-tear the repair and improve the number of patients having a successful outcome after rotator cuff repair. It is understood that the disclosed invention is not limited to rotator cuff repair, but merely used as an example for implementation purposes. Different from current arthroscopic surgical techniques that simply pass a single suture through the tissue, this invention will manipulate the tissue from begin flat so that a single suture is passed through the tissue more than one time. In addition, different from current arthroscopic surgical techniques that simply pass a single suture through the tissue, this invention will suture a loop through the tissue that another suture will pass through resulting in sewing both sides of the tissue.

For example, the tissue will be rolled, wrinkled, folded, bent, or tucked so that a needle can be placed through the tissue more than once. This will make it easier for the surgeon to perform more complex suture configurations. For example, sutures can be placed from top-to-bottom and bottom-to-top with a single pass of the needle.

In another embodiment, several arthroscopic sewing instruments will roll, wrinkle, fold, bend or tuck the flat tissue so that a needle can be placed through the tissue more than once. This will allow surgeons to place complex locking and grasping suture configurations that will significantly improve the quality of the repair.

BRIEF DESCRIPTION OF THE DRAWINGS

This disclosure is illustrated by way of example and not by way of limitation in the accompanying figure(s). The figure(s) may, alone or in combination, illustrate one or more embodiments of the disclosure. Elements illustrated in the figure(s) are not necessarily drawn to scale. Reference labels may be repeated among the figures to indicate corresponding or analogous elements.

The detailed description refers to the accompanying figures in which:

FIGS. 7A-7J illustrate implementation examples of one or more embodiments of the disclosed invention; and FIGS. 8A-8H illustrate implementation examples of one or more embodiments of the disclosed invention.

DETAILED DESCRIPTION OF THE INVENTION

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Figure 6A:
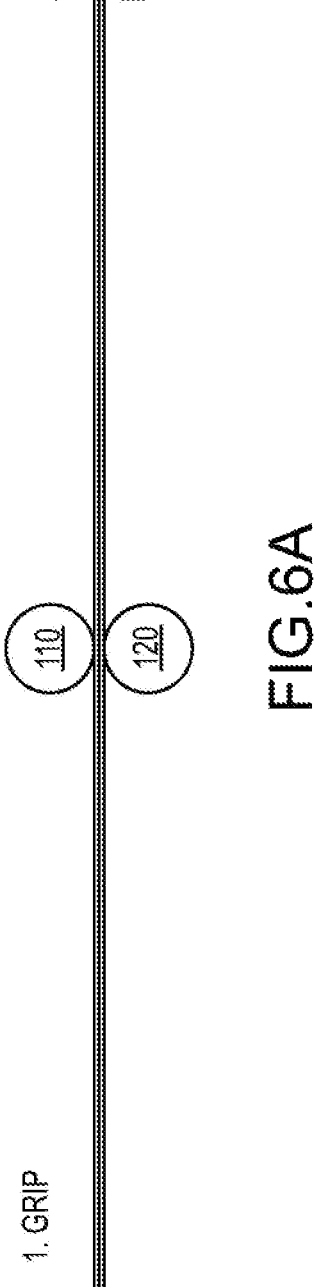
FIGS. 6A-6Z illustrate implementation examples of one or more embodiments of the disclosed invention.
Figures 6T, 6U, 6V:
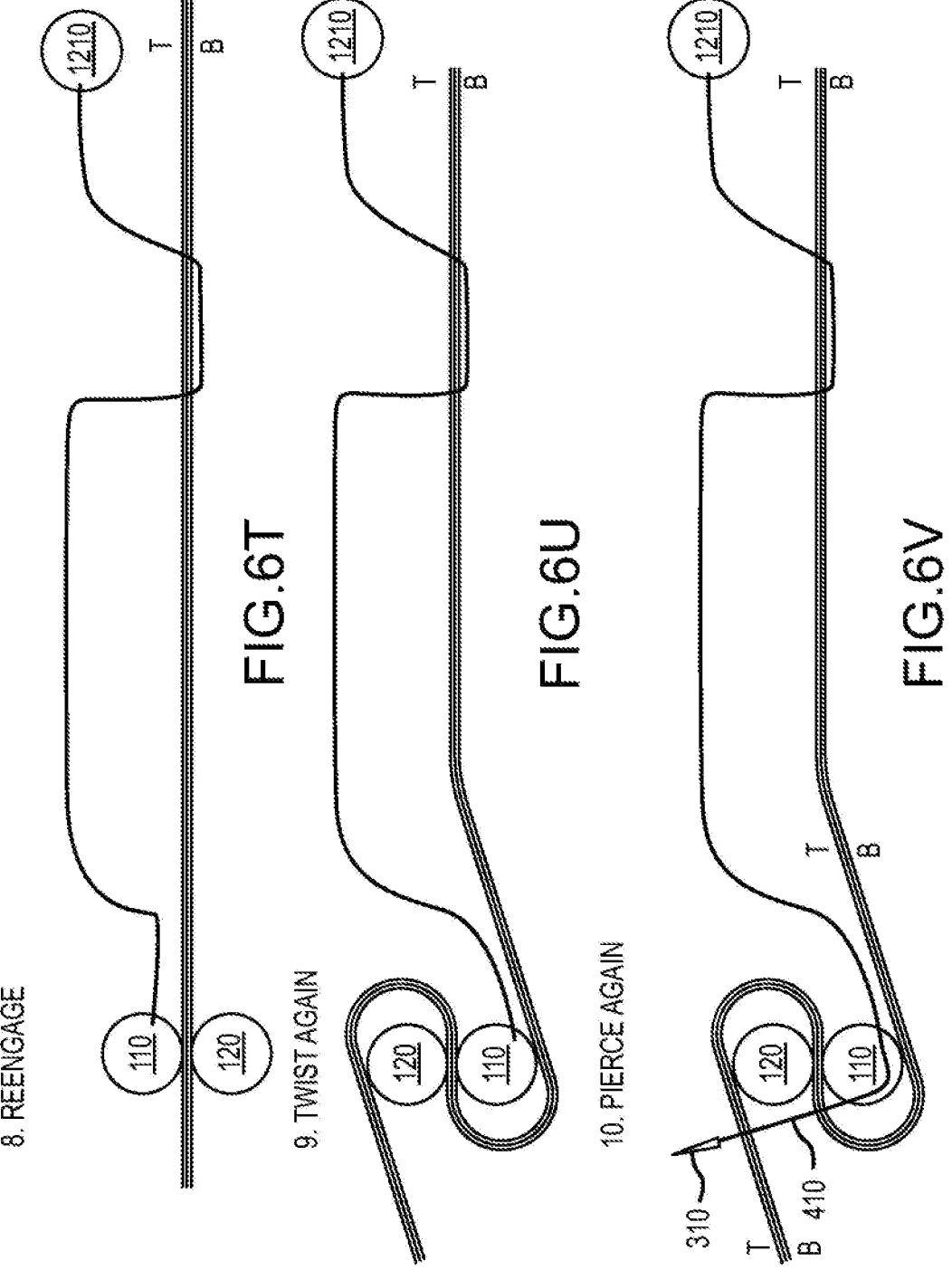
Figures 6W, 6X:
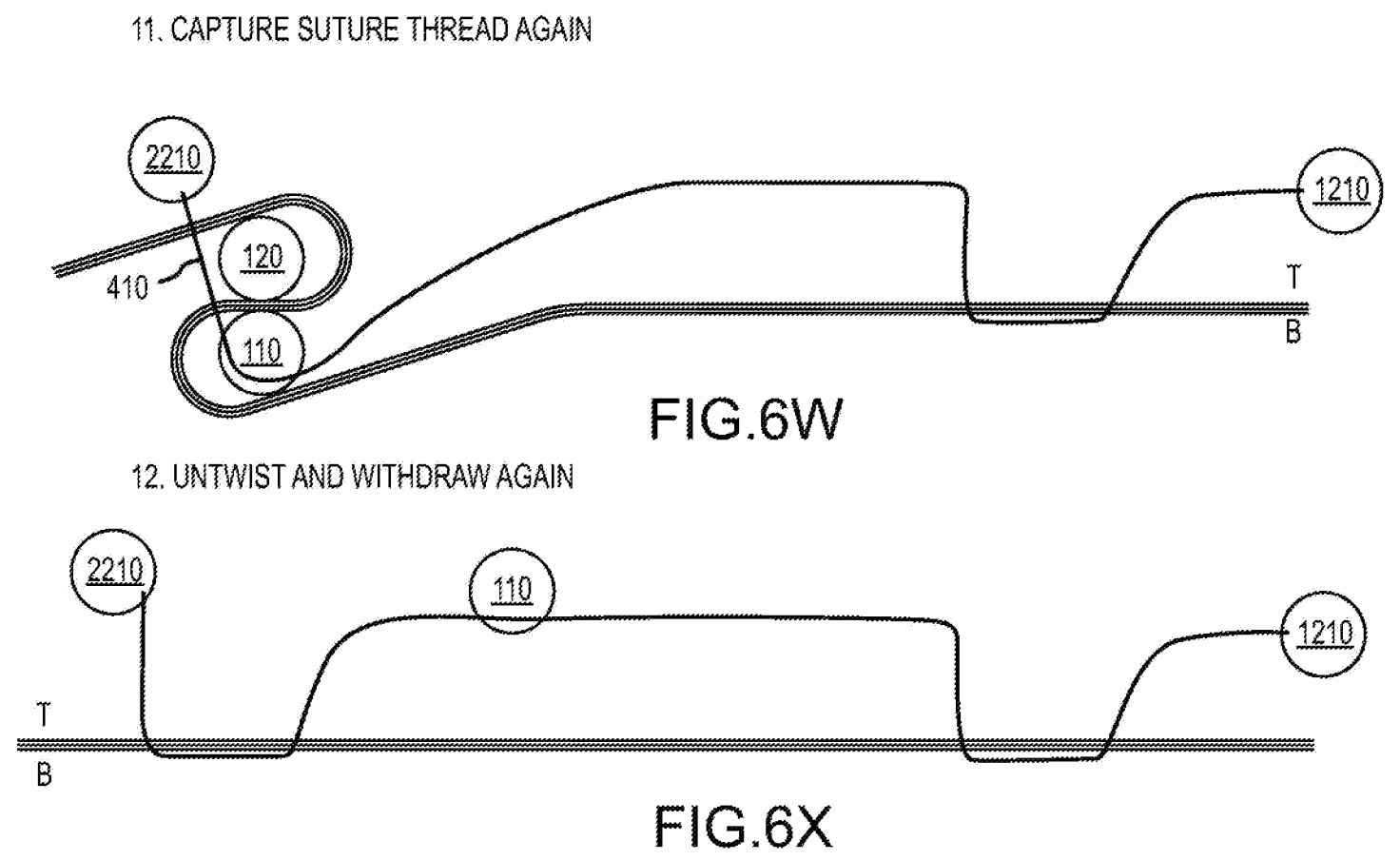
Figures 6Y, 6Z:
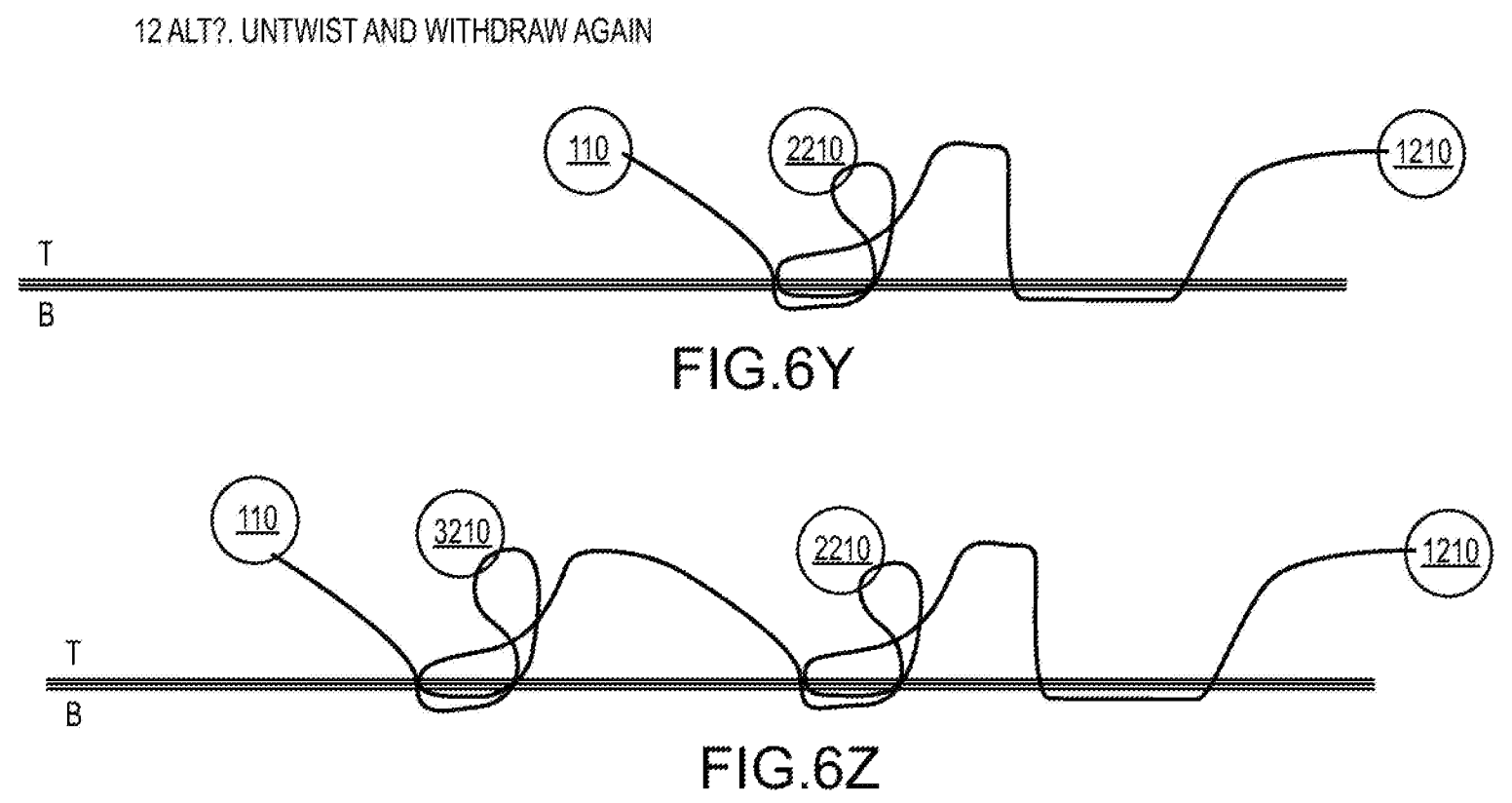

The first instrument has a tip (110) on the top of the tissue and another (120) on the bottom is shown in FIGS. 6A-6Z. The instrument grasps above and under the tissue as shown in FIG. 6B. The instrument then rolls the tissue 180 degrees such that 120 is on top and 110 is on the bottom as shown in FIGS. 6C and 6D. A flexible needle that can be offset in the tip to pass through either a small or a large amount of the fold created by the tissue being rolled will be passed through the rolled tissue from top to bottom and then from bottom to top as shown on the left of FIGS. 6F, 6G and 6H. The suture will then be caught by a third tip (1210) that slides onto the top of the tissue so that the suture can be pulled out. A second similar instrument will pass the suture through the rolled tissue from bottom to top and from top to bottom such that is has been passed bottom to bottom as shown on the right of FIGS. 61, 6J and 6K. In this instance, the second instrument essentially performs the same operations as the first instrument, just turned upside-down. This way, the surgeon will not be required to turn their hand upside down during the surgical procedure. The second instrument will have the hand piece positioned 180 degrees to the tip. The suture can be retracted as shown in FIGS. 6L and 6N. When the tissue is unrolled the suture has passed from top to bottom and then nearby from bottom to top as shown on the left in FIGS. 6P and 6R or from bottom to top and then top to bottom on the right as shown in FIGS. 6Q and 6S. The instrument can then be positioned a short distance away and the process repeated for a running stitch as shown in FIGS. 6T, 6U, 6V, 6W and 6X. The stitch can also be placed through a loop created in the running stitch as shown in FIGS. 6Y and 6Z for a running and locking stitch.

Figure 7A:
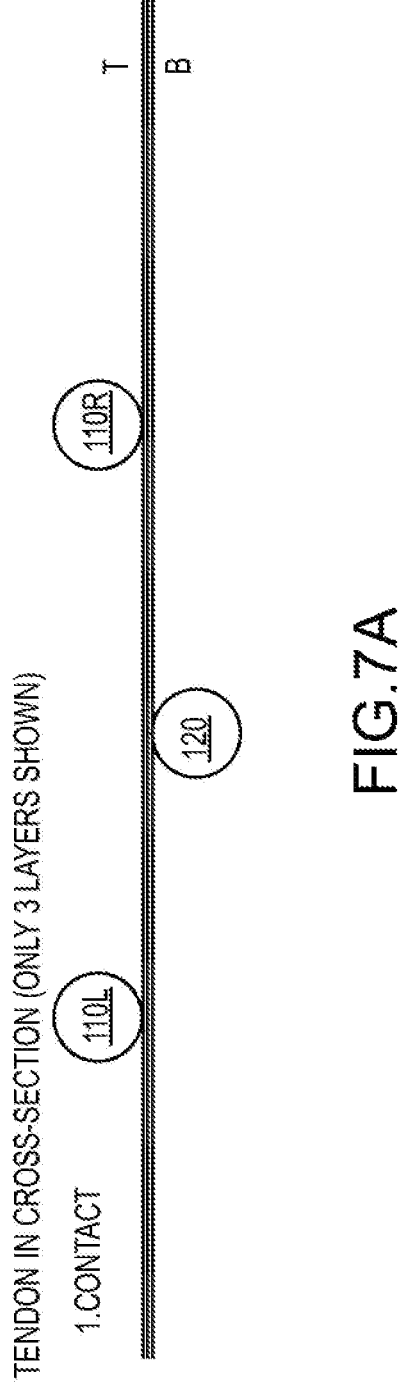
Figure 7B:
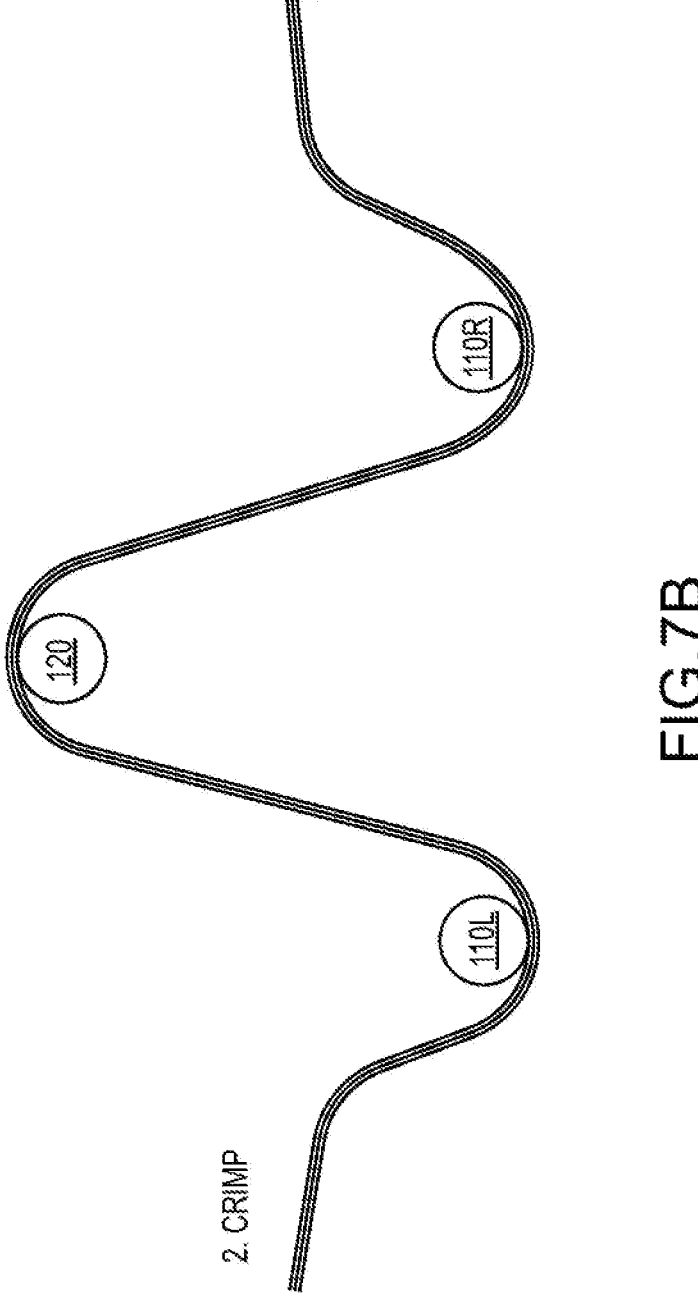
Figures 7C, 7D:
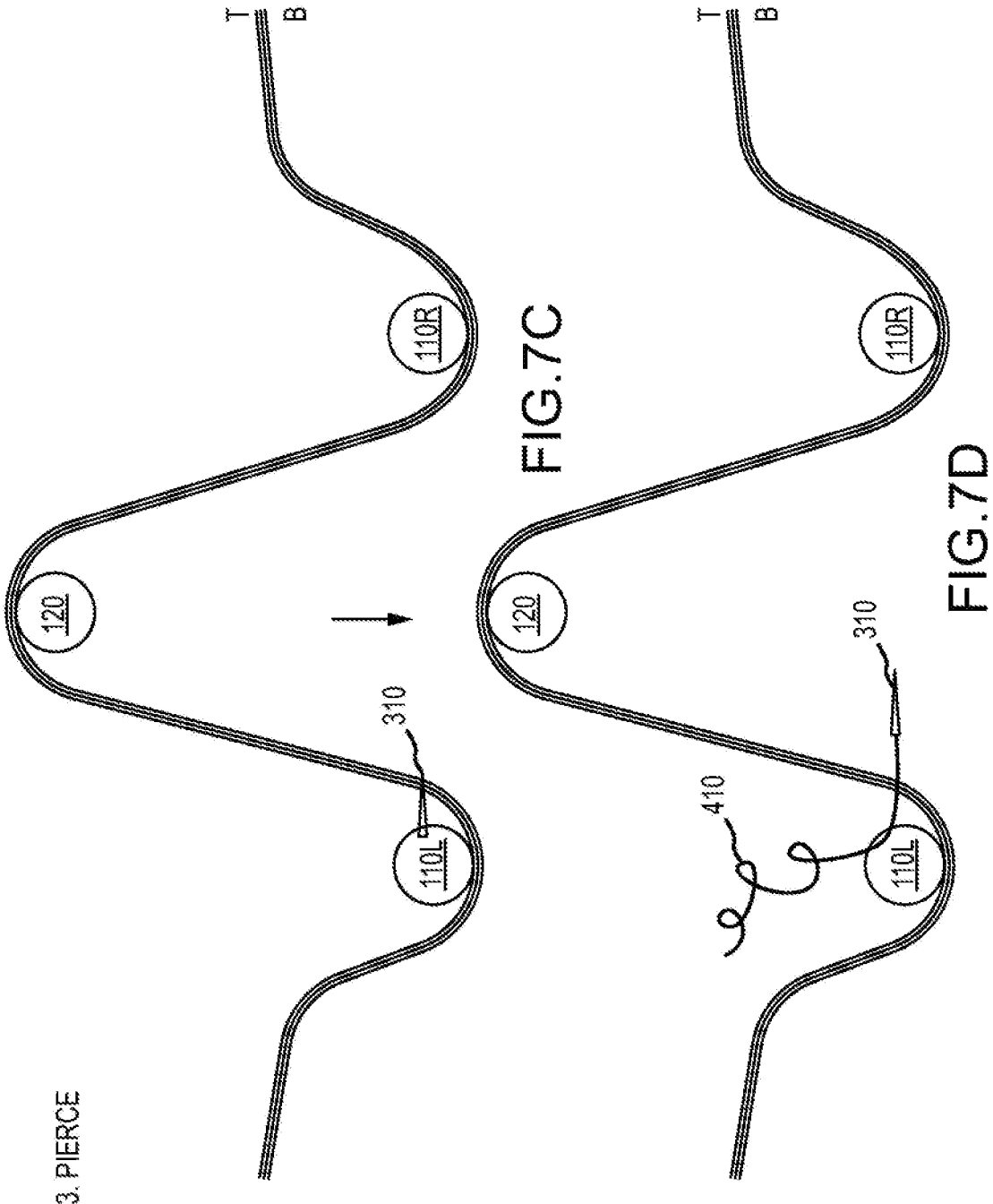
Figures 7E, 7F:
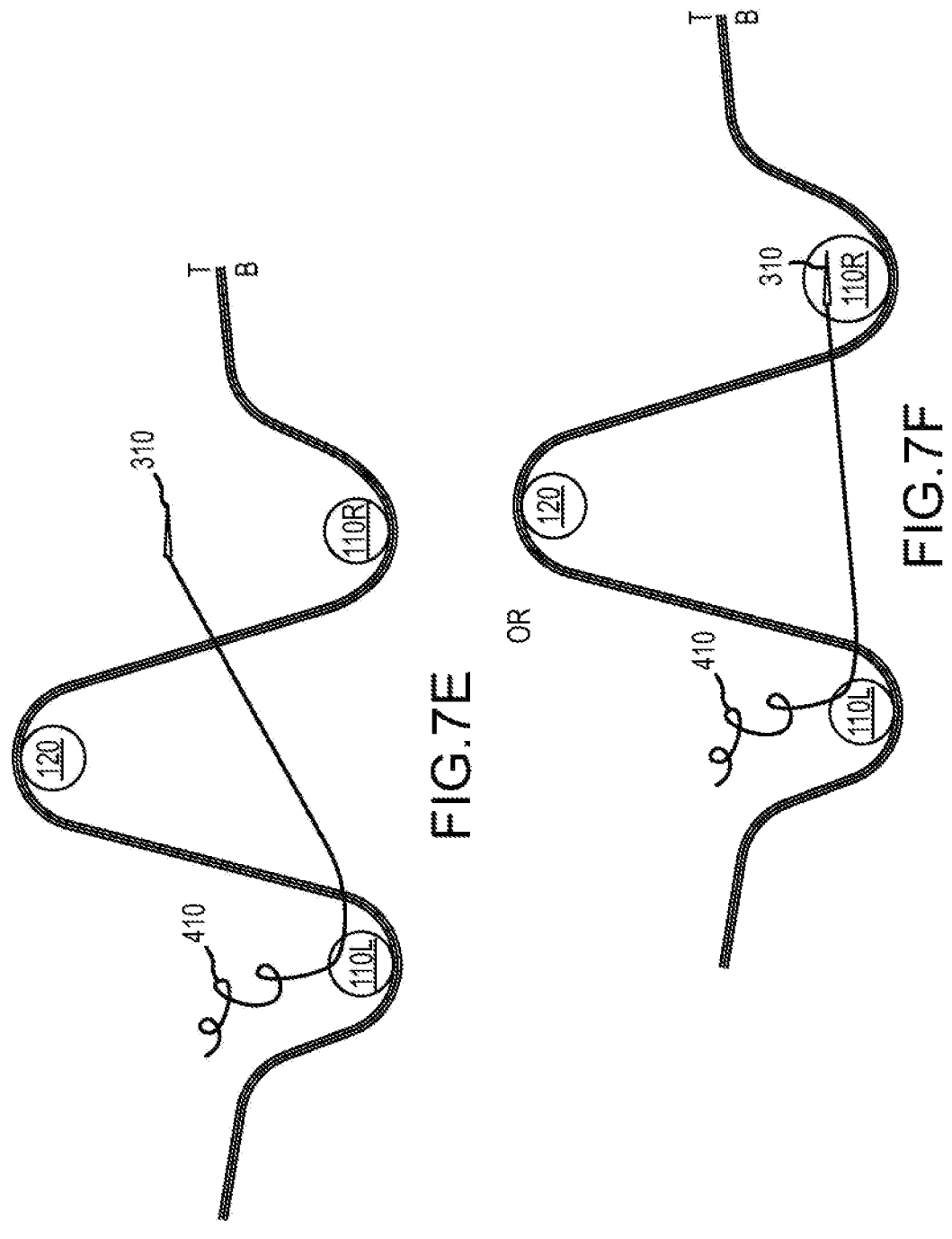

The third instrument is shown in FIG. 7A and it has 3 tips, one under the tissue (120) and 2 others, one on top on the left (110L) and another on top on the right (110R) side of the first. It will grasp above and under the tissue with one tip under and 2 tips above the tissue. Different from current sewing instruments the instrument will crimp the tissue so that the bottom tip is above those on the bottom as shown in FIG. 7B. A flexible needle that can be offset in the tip to pass through either a small or a large amount of the crimp from top to bottom through the tissue as shown in FIGS. 7C and 7D and then from bottom to top of the right side as shown in FIG. 7F and captured by the right tip as shown in FIG. 7F. When the tissue is uncrimped the suture has passed from top to bottom and then nearby from bottom to top as shown in FIG. 7G and it can be retracted as shown in FIG. 7H. The ends of the sutures can be withdrawn as shown in FIG. 7I and the needle prepared as shown in FIG. 7J so that it can then be positioned a short distance away and the process repeated for a running stitch. The fourth instrument is not depicted but it will work just like the third but with two tips on bottom and one on the top so that with the resulting crimp suture will be placed from bottom to top and then nearby from top to bottom.

Figure 8E:
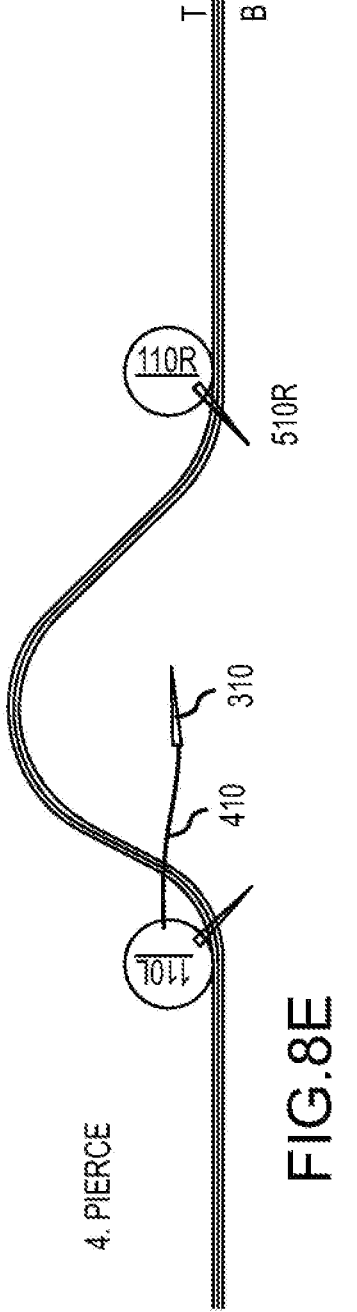
Figure 8F:
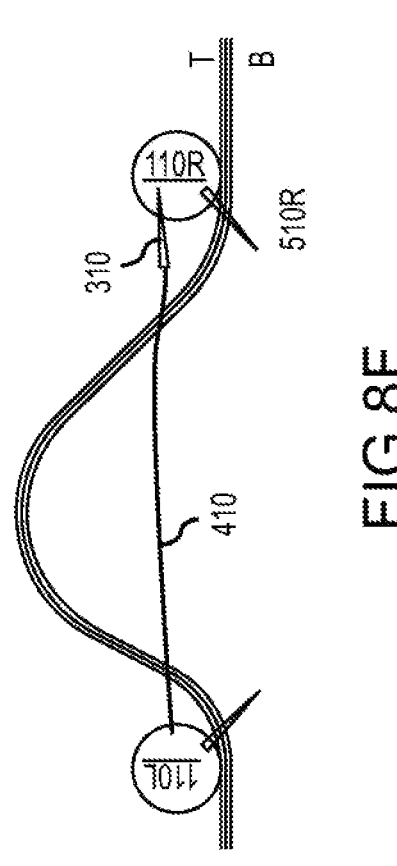

The fifth instrument may have tips with a small barb (510L and 510R) in each that will be placed a short distance apart into the top of the tissue (110L and 110R) as shown in FIGS. 8A and 8B. The tips will roll and come closer together as shown in FIGS. 8C and 8D to create a tuck on top of the tissue. A flexible needle that can be offset in the left tip to pass through either a small or a large amount of the tuck will pass a suture from top to bottom and then from bottom to top and captured from the tip on the left as shown in the FIGS. 8E and 8F. The tissue will then be untucked and the suture retracted as shown in FIGS. 8G and 8H. The sixth instrument is not depicted but it will work just like the fifth but with the barbs on the bottom of the tissue to create a tuck under the tissue.

A seventh instrument is not depicted but it will incorporate a combination of the $1^{st}$ and the $5^{th}$ instruments. It may have a tip with a small barb that can be placed into the top of the tissue and the tissue can then be rolled. A flexible needle can then pass through the rolled tissue so that it will pass a suture from top to bottom and then from bottom to top. The suture will then be caught by a second tip that slides onto the top of the tissue so that the suture can be pulled out. This instrument can also be under the tissue and the barb placed into the bottom of the tissue and the tissue can then be rolled. A flexible needle can then pass through the rolled tissue so that it will pass a suture from bottom to top and then from top to bottom. The suture will then be caught by a second tip that slides onto the bottom of the tissue so that the suture can be pulled out.

Figures 1A, 1B:
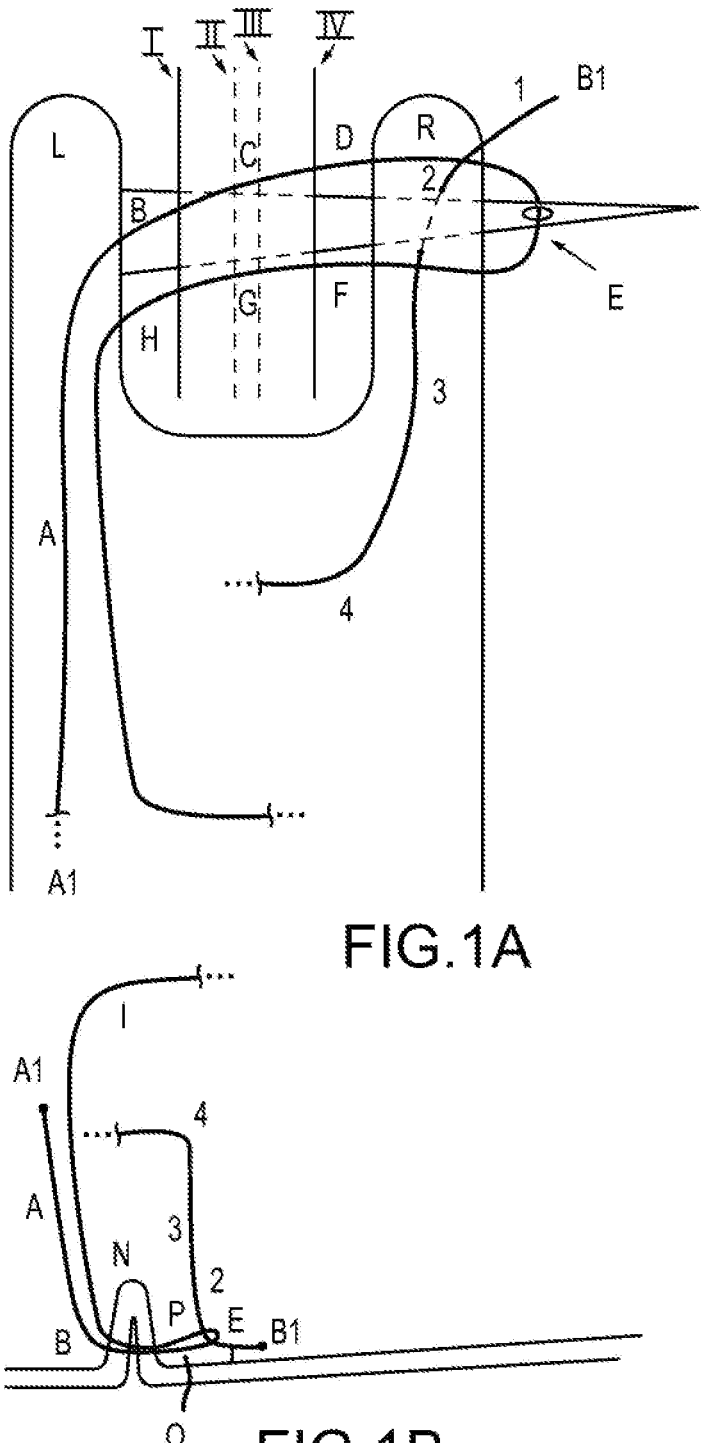
FIGS. 1A and 1B illustrate a tissue crimping device in accordance with at least one embodiment of the disclosed invention.

In FIGS. 1A and 1B, a surgical device is shown crimping tissue I, II, III, IV. The device (and just the crimped bit of tissue) are shown in the upper figure IA, and only the tissue and sutures are shown in the lower FIG. 1B. A flexible needle is extended from prong L of the device and interacts with prong R (passes into, through, or adjacent prong R). A first suture (on the left and marked with letters) passes through a closed eye on the needle at E (letters describe relative positions on the first suture). The first suture is anchored at A1 (outside the body or within the instrument-someplace a surgeon can get to later). The needle may be shaped or operated so that the first suture has an open portion (D-E-F). After the needle is deployed, the end (BI) of a second suture (on the right and marked with numbers is passed through the open portion of the first suture (either through a loop of the first suture or through a second hole in the needle) and that end (BI and 1) is captured, with a 'trap-door' type device. The second suture extends (1, 2, 3, 4 . . . ) into the device, so that it can be "unwound" and accessed later.

Figures 2A, 2B:
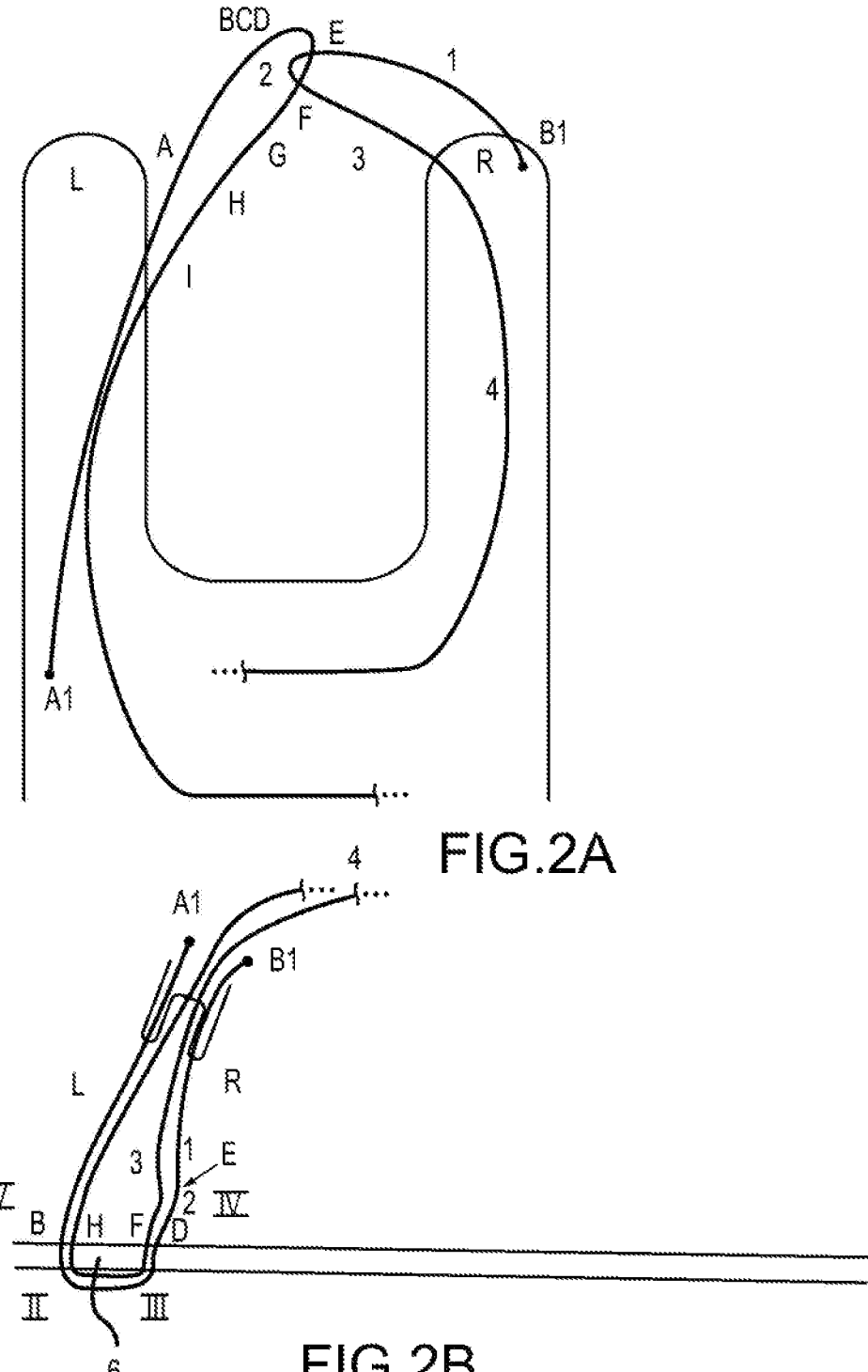
FIGS. 2A and 2B illustrate an embodiment wherein a needle is retracted and the tissue is uncrimped in accordance with at least one embodiment of the disclosed invention.

In FIGS. 2A and 2B, the needle is retracted and the tissue is uncrimped. The first suture (on the left and marked with letters) is anchored at A1, feeds through the device, loops around the second suture (on the right and marked with numbers) at E of the first suture, and feeds back into the device, which can now be repositioned. The second suture is anchored with a trap-door device at B1, loops around the first suture at 2, and feeds back into the device. The lower figure shows the resulting stitch, entering the tissue at roman numeral I, exiting at II, extending along the underside to III, and reemerging at IV. The surgeon could stop now with one stitch on top and one on the bottom.

Figures 3A, 3B:
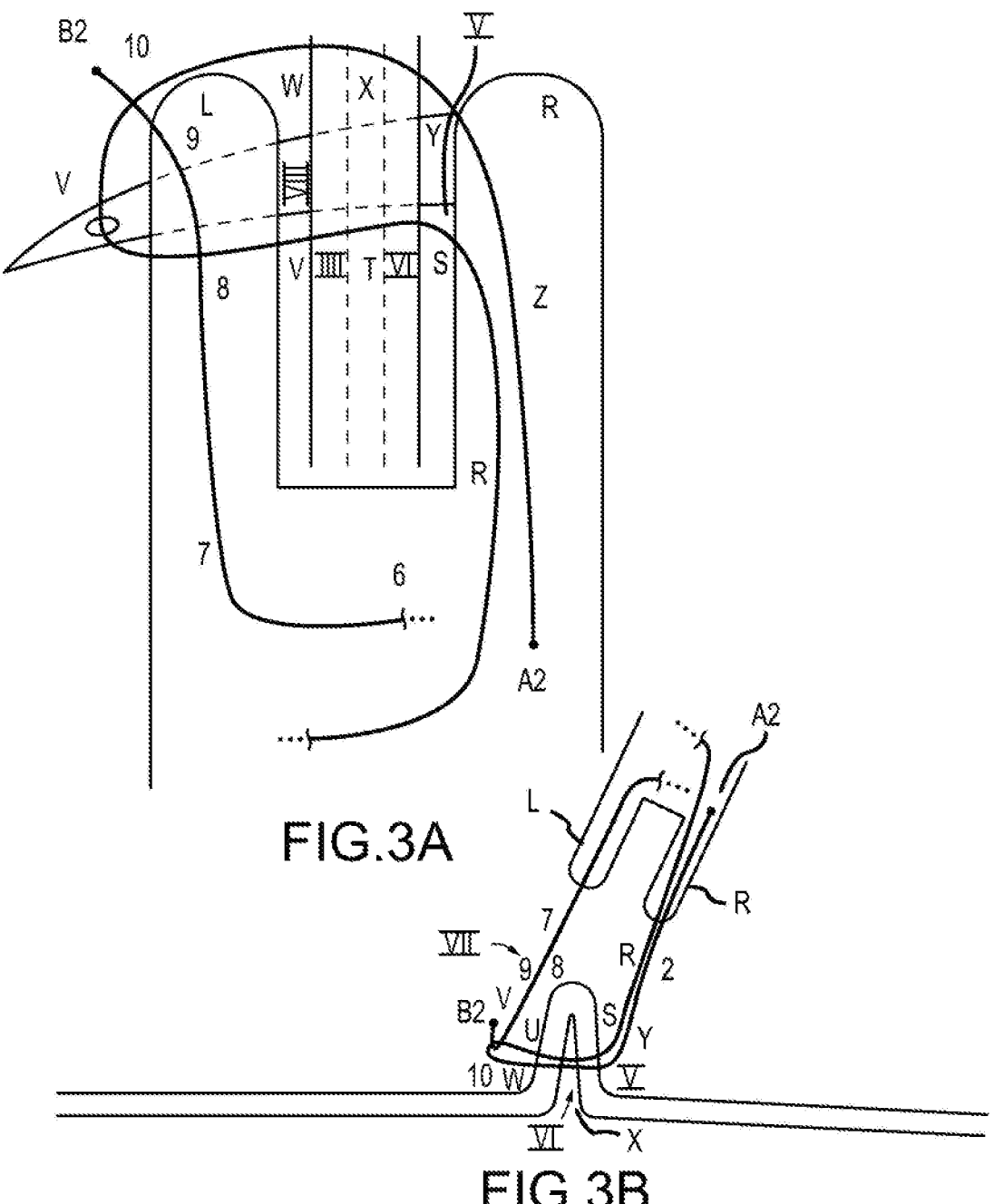
FIGS. 3A and 3B illustrate an embodiment where the device has been repositioned and crimps a different part of the same tissue in accordance with at least one embodiment of the disclosed invention.

In FIGS. 3A and 3B, the device has been repositioned and crimps a different part of the same tissue. As in FIGS. 1A and 1B (but in the opposite directions), a flexible needle bearing the first suture is extended from prong Rand interacts with prong L. The first suture (on the right and marked with letters) is anchored at A2, passes through the eye of the needle, and feeds back into prong R of the device. The second end of the second suture (on the left and marked with numbers) is passed through the open portion of the first suture, as before, and captured with a second 'trap-door' on prong L.

Figures 4A, 4B:
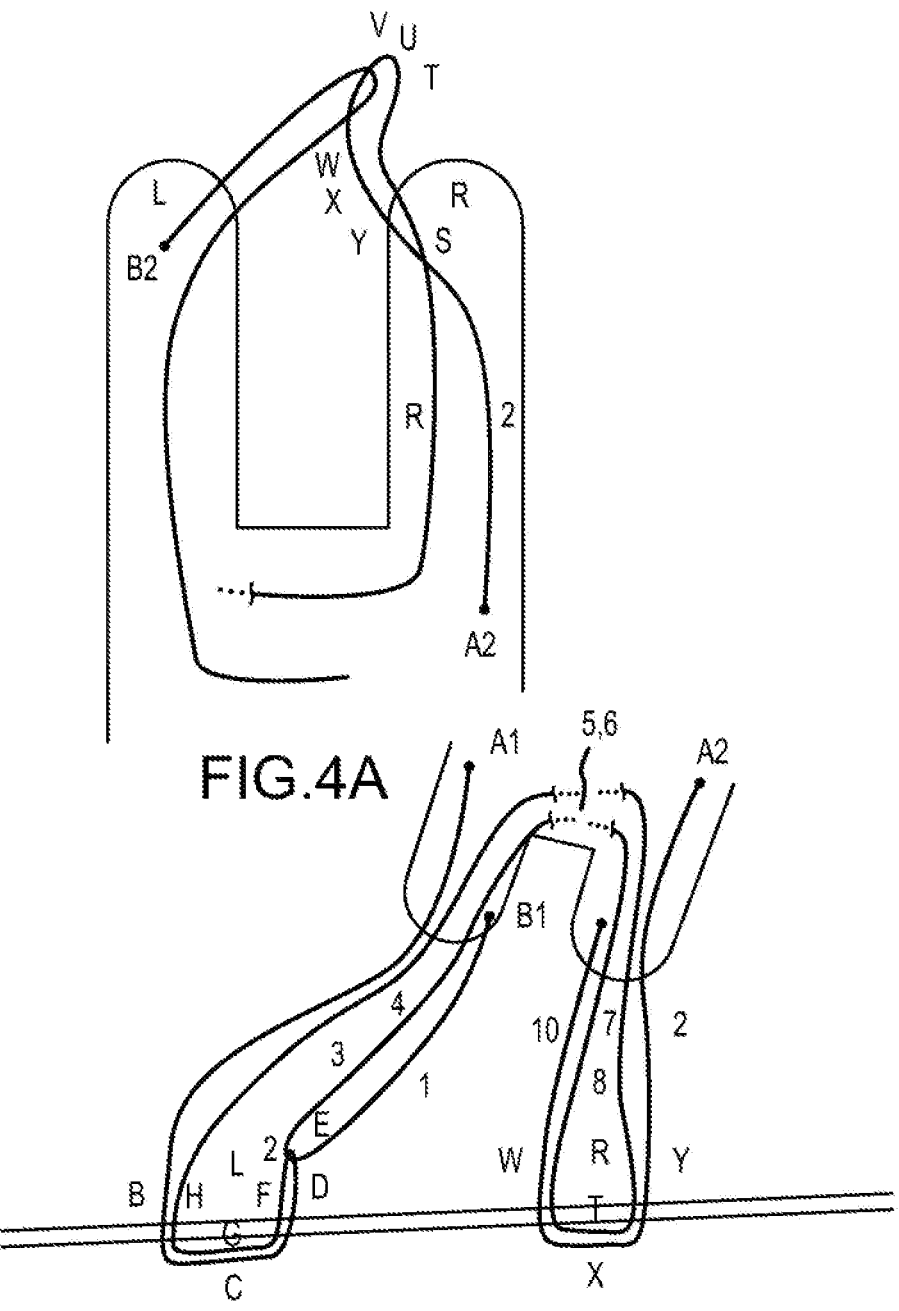
FIGS. 4A and 4B illustrate an embodiment where the needle from prong R has been retracted and the tissue is uncrimped again.

In FIGS. 4A and 4B, the needle from prong R has been retracted and the tissue uncrimped again. The device is withdrawn from the tissue. The first suture is anchored to the device at A1 and A2, but can "unspool" as the device is withdrawn (shown as a coil). Similarly, the second suture is anchored to the device at B1 and B2 and can unspool as the device is withdrawn. In another embodiment, the first and second sutures can actually be a pair of sutures (four total), rather than necessarily having to be the opposite ends of the same suture. The result is two pairs of mattress stitches, each having two leads extending from their insertion points. The leads can be tied as desired (e.g., some extending "straight down" and some extending "cross-wise" to yield a surface that conforms closely to the underlying surface.

Figure 5:
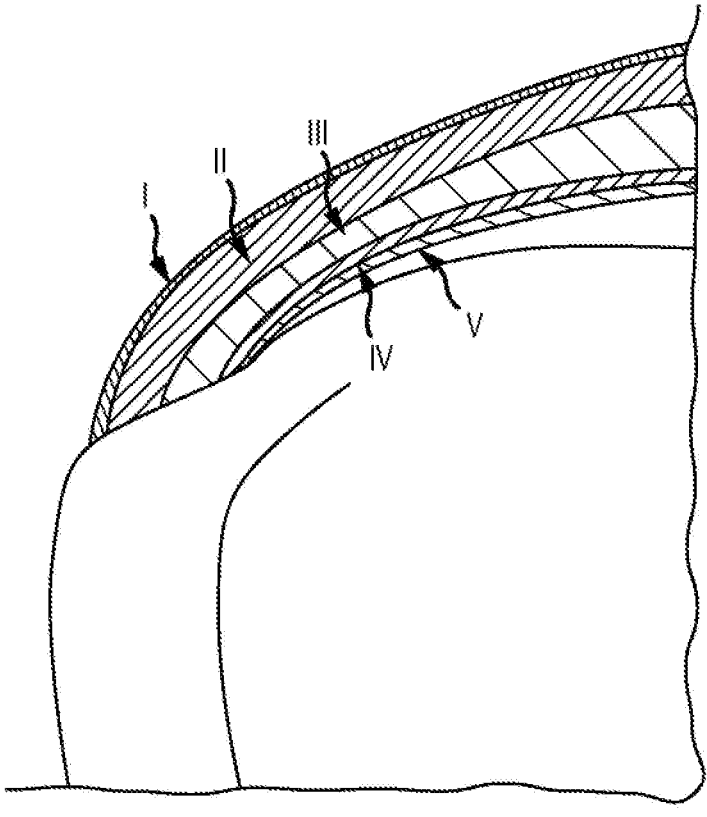
FIG. 5 is a 3-D graphic of the supraspinatus insertion corresponds to the coronal imaging plane and depicts the histologic layers of the cuff in accordance with at least one embodiment of the disclosed invention.

In view of FIG. 5, a 3D graphic of the supraspinatus insertion corresponds to the coronal imaging plane and depicts the histologic layers of the cuff. Layer I is the most superficial layer, measuring 1 mm in thickness and composed of fibers from the coracohumeral ligament which extend posteriorly and obliquely. Layer II is composed of densely packed fibers that parallel the long axis of the tissue and measures 3-5 mm in thickness. Layer III is 3 mm thick and composed of smaller bundles of collagen which are loosely organized at an approximately 45-degree angle to the long axis of the tissue. Layer IV is composed of loose connective tissue and thick collagen bands and merges with fibers from the coracohumeral ligament. Layer V represents the shoulder capsule and measures approximately 2 mm in thickness.

Layer I is the most superficial layer, measuring 1 mm in thickness and composed of fibers from the coracohumeral ligament which extend posteriorly and obliquely. Layer II is composed of densely packed fibers that parallel the long axis of the tissue and measures 3-5 mm in thickness. Layer III is 3 mm thick and composed of smaller bundles of collagen which are loosely organized at an approximately 45-degree angle to the long axis of the tissue. Layer IV is composed of loose connective tissue and thick collagen bands and merges with fibers from the coracohumeral ligament. Layer V represents the shoulder capsule and measures approximately 2 mm in thickness.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

What is claimed is:

1. A surgical instrument for placing complex sutures into animal tissues, the surgical instrument comprising:
   a first tip and a second tip operable to:
      grip a tissue; and
      roll the tissue;
   a needle configured to pass through a fold in the tissue created by the roll; and
   the first tip and the second tip configured to be separated by a first distance and at least one of the first tip and the second tip moveable along a plane to reduce the first distance;
   the first tip configured to pass the needle and a suture through the rolled tissue in a first direction that is nonparallel relative to the plane such that the needle and suture do not contact the second tip when the needle and suture pass through the rolled tissue.

2. The surgical instrument of claim 1, further comprising a third tip operable to receive the needle and suture.

3. The surgical instrument of claim 1, wherein the needle is a flexible needle.

4. The surgical instrument of claim 1, wherein the needle is offset to pass through a small amount of the folded tissue.

5. The surgical instrument of claim 1, wherein the needle is offset to pass through a large amount of the folded tissue.

6. The surgical instrument of claim 1, wherein the tissue is a fibrous tissue.

7. The surgical instrument of claim 1, wherein the surgical instrument is operable to perform rotator cuff surgery.

8. A surgical instrument for placing complex sutures into animal tissues having three tips:
   the first tip configured to be positioned under a tissue;
   the second tip configured to be positioned on top of the tissue and to the left of the first tip; and
   the third tip configured to be positioned on top of the tissue and to the right of the first tip;
   wherein the three tips have at least a first position in which the first tip resides outside of a plane extending between the second tip and the third tip and a second position in which the first tip resides on an opposite side of the plane relative to a location of the first tip when in the first position.

9. The surgical instrument of claim 8, wherein a needle is configured to be passed through the tissue when the three tips are in the second position.

10. The surgical instrument of claim 8, wherein the needle is a flexible needle.

11. The surgical instrument of claim 8, wherein the needle is configured to be passed from top to bottom of the tissue between the first and second tip.

12. The surgical instrument of claim 8, wherein the needle is configured to pass from bottom to top between the first and third tip.

13. A surgical instrument for placing complex sutures into animal tissues, the surgical instrument comprising:
   a first tip and a second tip;
   a first tip position in which the first tip is spaced apart from the second tip;
   the first tip operable to grip a tissue independent of the second tip or the second tip operable to grip the tissue independent of the first tip;
   a second tip position, the second tip position including at least one of the first tip and the second tip rotated relative to each other to create a fold in the tissue; and
   a needle connected to a suture, wherein the needle and suture are operable to pass through the fold in the tissue in at least one direction.

14. The surgical instrument of claim 13, further comprising a third tip operable to receive the needle and suture.

15. The surgical instrument of claim 13, wherein the needle is a flexible needle.

16. The surgical instrument of claim 13, wherein the needle is offset to pass through a small amount of the folded tissue.

17. The surgical instrument of claim 13, wherein the needle is offset to pass through a large amount of the folded tissue.

18. The surgical instrument of claim 13, wherein the tissue is a fibrous tissue.

* * * * *